(12) United States Patent
 Al Asoom (10) Patent No.: US 10,588,930 B2
(45) Date of Patent: Mar. 17, 2020

(54) **METHOD FOR EFFECTING ANGIOGENESIS BY ADMINISTERING *NIGELLA SATIVA***

(71) Applicant: Imam Abdulrahman Bin Faisal University, Dammam (SA)

(72) Inventor: Lubna Ibrahim A. Al Asoom, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 127 days.

(21) Appl. No.: 15/710,212

(22) Filed: Sep. 20, 2017

(65) Prior Publication Data
US 2019/0030110 A1   Jan. 31, 2019

Related U.S. Application Data

(60) Provisional application No. 62/539,028, filed on Jul. 31, 2017.

(51) Int. Cl.
*A61K 36/71* (2006.01)
*A61K 9/00* (2006.01)

(52) U.S. Cl.
CPC ............ *A61K 36/71* (2013.01); *A61K 9/0053* (2013.01); *A61K 9/0095* (2013.01)

(58) Field of Classification Search
CPC ..... A61K 36/71; A61K 9/0053; A61K 9/0095
See application file for complete search history.

(56) References Cited

U.S. PATENT DOCUMENTS

| 9,056,119 B2 | 6/2015 | Kameyama et al. |
| 9,180,155 B2 | 11/2015 | Babish et al. |
| 2011/0244060 A1 | 10/2011 | Ismail et al. |
| 2015/0004266 A1* | 1/2015 | Babish .................. A61K 36/71 424/776 |

FOREIGN PATENT DOCUMENTS

CN        105362372 A        3/2016

OTHER PUBLICATIONS

Seif, A. A., J. Physiol. Biochem., 2013, vol. 69, p. 937-944.*
Nagat et al., JBC, 2003, vol. 278, No. 33, Aug. 15 Issue, p. 31000-31006.*
Murukesh et al., British Journal of Cancer, 2010, vol. 102, p. 8-18.*
Al Asoom, L.I., "Coronary Angiogenic Effect of Long Term Administration of *Nigella sativa*", URL: https://www.omicsonline.org/2155-9880/2155-9880.C1.048_004.pdf; Journal of Clinical and Experimental Cardiology, vol. 7, Issue 8, 1 Page total (Sep. 13, 2016).

* cited by examiner

*Primary Examiner* — Kade Ariani
(74) *Attorney, Agent, or Firm* — Oblon, McClelland, Maier & Neustadt, L.L.P.

(57) ABSTRACT

A method for effecting angiogenesis in a subject at risk of or experiencing ischemia related to the heart, brain, kidney, intestine, and/or legs. The method involves administering *Nigella sativa* to the subject. The method may also treat ischemia.

20 Claims, 2 Drawing Sheets

METHOD FOR EFFECTING ANGIOGENESIS BY ADMINISTERING *NIGELLA SATIVA*

CROSS REFERENCE TO RELATED APPLICATIONS

This application claims the benefit of U.S. Provisional Application No. 62/539,028 filed Jul. 31, 2017, which is incorporated herein by reference in its entirety.

STATEMENT REGARDING PRIOR DISCLOSURE BY THE INVENTOR

Aspects of this technology are described in a conference abstract "Coronary angiogenic effect of long term administration of *Nigella sativa*" by Lubna Ibrahim Al Asoom, in J Clin Exp Cardiolog, 2016, 7:8, which is incorporated herein by reference in its entirety.

BACKGROUND

Field of the Disclosure

This disclosure relates to a method for effecting angiogenesis in a subject in need thereof. The method may treat ischemia related to the heart, brain, kidney, legs, and/or intestine.

Description of the Related Art

Coronary artery disease (CAD) is one of the leading causes of death worldwide. The World Health Organization (WHO) reports that 31% of deaths across the globe are due to cardiovascular diseases, and ischemic heart disease accounts for 46% of deaths from CAD (Alwan A, Armstrong T, Bettcher D, Boerma T, Branca F, Ho J, et al. Global atlas on cardiovascular disease prevention and control Policies, strategies and interventions. WHO; World Heart Federation; World Stroke Organization, 2011, incorporated herein by reference in its entirety). Risk factors of coronary artery disease include obesity, hypercholesterolemia, hypertension, diabetes, and smoking (Mack M, Gopal A. Epidemiology, Traditional and Novel Risk Factors in Coronary Artery Disease. Heart Fail Clin. 2016 Jan.; 12(1):1-10. PubMed PMID: 26567971, incorporated herein by reference in its entirety).

Exercise has been recommended as a cardiovascular protective measure. Favorable cardiac and coronary adaptations are well known to result from exercising, and they have been reported in the literature (Brown M D. Exercise and coronary vascular remodelling in the healthy heart. Exp Physiol. 2003 September; 88(5):645-58. PubMed PMID: 12955165; and Bernardo B C, McMullen J R. Molecular Aspects of Exercise-induced Cardiac Remodeling. Cardiol Clin. 2016 November; 34(4):515-30. PubMed PMID: 27692221, each incorporated herein by reference in their entirety). Exercise can enhance myocardial blood flow through multiple structural and physiological alterations of the coronary vascular bed. This includes increase in size of the conduit of large arteries, increases in the number of arterioles and induction of capillary growth (Tomanek R J. Exercise-induced coronary angiogenesis: a review. Med Sci Sports Exerc. 1994 Oct.; 26(10):1245-51. PubMed PMID: 7528318, incorporated herein by reference in its entirety). A wide range of stimuli have been suggested to explain the angiogenic effect of exercise training. During short bouts of exercise, the increased myocardial blood flow leads to increased shear stress and the release of endothelial vasodilators and nitric oxide (Zhang J, Friedman M H. Adaptive response of vascular endothelial cells to an acute increase in shear stress frequency. Am J Physiol Heart Circ Physiol. 2013 September; 305(6):H894-902. PubMed PMID: 23851277. Pubmed Central PMCID: PMC3761335, incorporated herein by reference in its entirety). Growth factors, such as fibroblast growth factors (FGFs), vascular endothelial growth factor (VEGF), and insulin growth factor-I (IGF-I), have been found to be upregulated in the coronary circulation in exercise-trained animals (Smith S K. Angiogenesis, vascular endothelial growth factor and the endometrium. Hum Reprod Update. 1998 1998 September-October; 4(5):509-19. PubMed PMID: 10027603, incorporated herein by reference in its entirety).

The method of assessing the increase in the coronary circulation in humans and animals which exercised varies. In exercise-trained human subjects and athletes, coronary circulation capacity is assessed by evaluating coronary flow, using electromagnetic flowmeter or ultrasonic devices (Papanastasiou G, Williams M C, Dweck M R, Alam S, Cooper A, Mirsadraee S, et al. Quantitative assessment of myocardial blood flow in coronary artery disease by cardiovascular magnetic resonance: comparison of Fermi and distributed parameter modeling against invasive methods. J Cardiovasc Magn Reson. 2016; 18(1):57. PubMed PMID: 27624746. Pubmed Central PMCID: PMC5022209, incorporated herein by reference in its entirety). In animals, immunohistochemical studies are used to label the vascular tree and measure the cross-sectional area (Marini M, Falcieri E, Margonato V, Treré D, Lapalombella R, di Tullio S, et al. Partial persistence of exercise-induced myocardial angiogenesis following 4-week detraining in the rat. Histochem Cell Biol. 2008 April; 129(4):479-87. PubMed PMID: 18172661, incorporated herein by reference in its entirety).

Despite accumulating evidence of the prophylactic influence of exercise on cardiac health and coronary circulation, the compliance toward exercise is low worldwide. Adjuvant therapeutics aimed to induce angiogenesis are needed either as prophylaxis of ischemia or as an attempt to rescue ischemic tissue.

An objective of the present disclosure is to provide a method for inducing angiogenesis and optionally treat ischemia.

SUMMARY

A first aspect of the disclosure relates to a method for effecting angiogenesis and optionally treating ischemia, the method comprising administering a first effective amount of *Nigella sativa* to a subject in need thereof.

In one embodiment, the method effects angiogenesis in at least one body part of the subject selected from the group consisting of a heart, a brain, and a limb.

In one embodiment, the method treats ischemia which is at least one selected from the group consisting of brain ischemia, ischemic heart disease, and limb ischemia.

In one embodiment, the method treats at least one type of ischemic heart disease selected from the group consisting of stable angina, myocardial infarction, cardiac syndrome X, and cardiac arrest.

In one embodiment, the method effects angiogenesis in a heart of the subject and does not lead to cardiac hypertrophy in the subject.

In one embodiment, the first effective amount of *Nigella sativa* is administered in a composition comprising water and *Nigella sativa* seeds.

In one embodiment, the composition comprises 1-50 wt % *Nigella sativa* seeds, based on a total weight of the composition.

In one embodiment, the *Nigella sativa* seeds are ground.

In one embodiment, the first effective amount of *Nigella sativa* is administered 1-3 times a day.

In one embodiment, the first effective amount of *Nigella sativa* is administered for 6-30 weeks.

In one embodiment, the first effective amount of *Nigella sativa* is administered 4-6 days per week for 7-10 weeks.

In one embodiment, the first effective amount of *Nigella sativa* is administered for 4-6 consecutive days per week.

In one embodiment, the first effective amount of *Nigella sativa* is in a range of 0.1-1 g/kg body weight of the subject.

In one embodiment, the first effective amount of *Nigella sativa* is in a range of 0.6-0.9 g/kg body weight of the subject.

In one embodiment, the first effective amount of *Nigella sativa* is administered orally.

In one embodiment, the method further comprises measuring a level of at least one biomarker selected from the group consisting of VEGF, VWF, PECAM-1, and NOS-2 before and/or after the administering of the first effective amount.

In one embodiment, the method further comprises administering a second effective amount of *Nigella sativa*.

In one embodiment, the second effective amount of *Nigella sativa* is in a range of 0.1-1 g/kg body weight of the subject and is different from the first effective amount of *Nigella sativa*.

In one embodiment, the second effective amount of *Nigella sativa* is administered for 1 day or 2-10 consecutive days.

In one embodiment, the second effective amount of *Nigella sativa* is administered for 4-6 consecutive days.

BRIEF DESCRIPTION OF THE DRAWINGS

A more complete appreciation and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Embodiments of the present disclosure will now be described more fully hereinafter with reference to the accompanying drawings, in which some, but not all embodiments of the disclosure are shown.

As used herein, the words "a", "an", and the like carry the meaning of "one or more". Within the description of this disclosure, where a numerical limit or range is stated, the endpoints are included unless stated otherwise. Also, all values and subranges within a numerical limit or range are specifically included as if explicitly written out.

Ischemia is a restriction in blood supply to tissues, causing a shortage of oxygen and glucose needed for cellular metabolism. Ischemia can be partial (e.g., 20% to less than 100%, 30-80%, or 40-60% of an initial total blood supply) or total. Ischemia may be caused by atherosclerosis, which is the deposition and hardening of plaque on the walls of the arteries, thus narrowing or blocking the arteries. The plaque contains cholesterol, fat, and calcium.

As oxygen is carried to tissues in the blood, insufficient blood supply causes tissue to become starved of oxygen. In the highly aerobic tissues of the heart and brain, irreversible damage to tissues can occur in as quickly as 3-4 minutes at body temperature.

Ischemic heart disease is a condition that affects the supply of blood to the heart. Ischemic heart disease may be stable angina, unstable angina, myocardial infarction, cardiac syndrome X, or cardiac arrest.

Brain ischemia is a condition in which there is insufficient blood flow to the brain to meet metabolic demand. This condition leads to poor oxygen supply or cerebral hypoxia and eventually the death of brain tissue or ischemic stroke. There are two types of brain ischemia: (1) focal ischemia, which is confined to a specific region of the brain; and (2) global ischemia, which encompasses wide areas of brain tissue.

Peripheral artery disease (PAD) is a narrowing of the arteries other than those that supply the heart or the brain. Peripheral artery disease most commonly affects the legs and includes acute limb ischaemia, critical limb ischemia, renal ischemia, chronic mesenteric ischemia, and acute mesenteric ischemia.

As used herein, the term "effect angiogenesis" in a subject in need thereof refers to inducing a physiological process in which new blood vessels form from pre-existing vessels. The formation of new blood vessels may be indicated by: (1) an increase in a level of at least one angiogenic protein (including several growth factors) such as fibroblast growth factor (FGF), vascular endothelial growth factor (VEGF), vascular endothelial growth factor receptor (VEGFR), neuropilin-1 (NRP-1), angiopoietin 1 (Ang1), angiopoietin 2

(Ang2), platelet-derived growth factor (PDGF), platelet-derived growth factor receptor (PDGFR), transforming growth factor beta (TGF-β), transforming growth factor beta receptor, endoglin, chemokine ligand 2 (CCL2), integrins $\alpha_v\beta_3$, $\alpha_v\beta_5$ and $\alpha_5\beta_1$, vascular endothelial cadherin, platelet endothelial cell adhesion molecule (PECAM-1), ephrin, plasminogen activators, plasminogen activator inhibitor-1, nitric oxide synthase 3 (eNOS), cyclooxygenase-2 (COX-2), AC133, DNA-binding protein inhibitor ID-1, DNA-binding protein inhibitor ID-3, and class 3 semaphorins. The increase in the level of the angiogenic protein may be at least 30%, 40%, 50%, 60%, 70%, or 80%, relative to an initial angiogenic protein level or an angiogenic protein level of a healthy subject (i.e., one who is not treated with *Nigella sativa*). In some embodiments, the increase in the angiogenic protein level may be accompanied by a reduction in a von Willebrand factor (VWF) level (by at least 30%, 40%, 50%, 60%, 70%, or 80%) relative to an initial VWF level or a VWF level in a healthy subject.

As used herein, the terms "treat", "treatment", and "treating" in the context of the administration of a therapy to a subject in need thereof refer to the reduction or inhibition of the progression and/or duration of a disease, the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g., by more than 10%, 20%, 30%, 40%, 50%, preferably by more than 60% of the plaque in the arteries before administration), or elimination of plaque; (2) inhibiting plaque buildup in arteries; (3) relieving to some extent (or, preferably, eliminating) one or more symptoms associated with a pathology related to or caused in part by plaque buildup in arteries; (4) an increase in disease-free, relapse-free, progression-free, and/or overall survival, duration, or rate; (5) a decrease in hospitalization rate; (6) a decrease in hospitalization length; (7) a stabilization or reduction in the rate of plaque buildup (e.g. by at least 10%, 20%, 30%, 40%, 50%, 60%, 70%, preferably at least 80%) relative to the initial rate of plaque buildup in the arteries; (8) a reduction in the amount of calcium in the arteries (e.g. by at least 10%, 20%, 30%, 40%, 50%, 60%, 70%, preferably by at least 80%) relative to the initial amount of calcium; (9) a reduction in the total cholesterol level in the blood (e.g. by at least 10%, 20%, 30%, 40%, 50%, 60%, 70%, preferably by at least 80%) relative to the initial total cholesterol level; (10) an impairment in the formation of plaque in the arteries; (11) a reduction in mortality; (12) a decrease in the need for surgery; and (13) increase in blood supply to the heart, brain, legs, kidney, and/or intestine (by at least 10%, 20%, 30%, 40%, 50%, 60%, 70%, preferably by at least 80%) relative to the initial blood supply.

In the context of the disclosure, the term "arteries" refers to arteries of the heart, brain (e.g., anterior cerebral artery, middle cerebral artery, and posterior cerebral artery), leg (e.g., femoral artery), kidney, and/or small intestine.

The results may be observed with methods such as a physical exam, blood test, electrocardiogram, chest X-ray, ankle/brachial index, echocardiography, computed tomography scan, stress testing, angiography, electromagnetic flowmeter, Doppler ultrasound, magnetic resonance imaging (MRI), and positron emission tomography (PET). For example, the increase in blood supply may be due to angiogenesis which may be determined by single photon emission computed tomography (SPECT) imaging and/or thrombolysis in myocardial infarction (TIMI) myocardial perfusion grade. In other embodiments, the increase in blood supply may be due to the reduction/removal of plaque from the arteries.

The terms "patient", "subject", and "individual" are used interchangeably. As used herein, they refer to individuals suffering from a disease and encompass mammals and non-mammals. None of the terms require that the individual be under the care and/or supervision of a medical professional. Mammals are any member of the mammalian class, including but are not limited to humans, non-human primates, such as chimpanzees, and other apes and monkey species, farm animals, such as cattle, horses, sheep, goats, swine, domestic animals, such as rabbits, dogs, and cats, laboratory animals including rodents, such as rats, mice and guinea pigs, and the like. Examples of non-mammals include, but are not limited to, birds, fishes, frogs, and the like. In preferred embodiments, the subject is a human. In some embodiments, the subject is a laboratory rat such as a biobreeding rat, a Brattleboro rat, a hairless rat, a knockout rat, a Lewis rat, a Long-Evans rat, a Royal College of Surgeons (RCS) rat, a shaking rat Kawasaki, a Sprague Dawley rat, a Wistar rat, or a Zucker rat. The rat may be male or female. The age of the rat may be between 1-5 months, 1.5-4 months, or 2-3 months. In some embodiments, a weight of the rat falls within a healthy range of 100-400 g, 150-350 g, or 200-300 g. In some embodiments, the rat is overweight and weighs more than 400 g to 1.2 kg, 500-950 g, or 700-800 g. In preferred embodiments, the laboratory rat is a Wistar rat.

A subject in need of treatment includes a subject already with the disease, a subject which does not yet experience or exhibit symptoms of the disease, and a subject predisposed to the disease. In preferred embodiments, the subject is a person who is predisposed to ischemia, e.g. a person with high cholesterol levels and/or high blood pressure, sleep apnea, diabetes, and high blood triglyceride levels; a person who is overweight/obese, smokes, and/or has a sedentary lifestyle; or a person with a family history of high cholesterol and/or high blood pressure.

In another embodiment, the subject refers to a patient who has undergone surgery (e.g., percutaneous coronary intervention (also known as coronary angioplasty), artery bypass, stenting, and carotid endarterectomy) to treat atherosclerosis and/or ischemia.

*Nigella sativa* (also known as black seed) is a herb used as a traditional remedy in the Arab countries, Iran, Tunisia, and India. It received its name from the appearance of the seeds which are small (1-5 mg in weight) and have dark grey to black color (Kokoska L, Havlik J, Valterova I, Sovova H, Sajfrtova M, Jankovska I. Comparison of chemical composition and antibacterial activity of *Nigella sativa* seed essential oils obtained by different extraction methods. J Food Prot. 2008 December; 71(12):2475-80. PubMed PMID: 19244901, incorporated herein by reference in its entirety). Generically, it is known as *Nigella sativa* Linn.

Broadly, *Nigella sativa* seeds contain 28-40%, 32-38%, or 36-38% fixed oil, 20-28% proteins, alkaloids (e.g., isoquinoline alkaloid—nigellicimine and nigellicimine n-oxide; pyrazol alkaloid—nigellidine and nigellicine), saponin, and 0.1-3%, 0.2-2.8%, or 0.4-2.5% essential oil, based on a total weight of the seeds. The composition of *Nigella sativa* grown in different parts of the world is listed in Table 1.

TABLE 1

Comparison of the composition of *Nigella sativa* obtained from Saudi Arabia, Iran, and Tunisia

|  | Saudi Arabia | Iran | Tunisia |
| --- | --- | --- | --- |
| Protein | 20.85% | 22.6%, | 26.7% |
| Fixed and essential oil | 38.20% | 40.35% | 28.48% |
| Ash | 4.37% | 4.41% | 4.86% |
| Total carbohydrate | 31.94% | 32.7% | 40.0% |

The fixed oil contains mainly of unsaturated fatty acids, including arachidonic acid, eicosadienoic acid, linoleic acid, linolenic acid, oleic acid, palmitoleic acid, palmitic acid, stearic acid, and myristic acid. The fixed oil also contains beta-sitosterol, cyclocucalenol, cycloartenol, sterol esters, and sterol glucosides. The composition of the fixed oil from *Nigella sativa* grown in different parts of the world is listed in Table 2.

TABLE 2

Comparison of the composition of fixed oil *Nigella sativa* obtained from Saudi Arabia, Iran, and Tunisia

|  | Saudi Arabia | Tunisia | Iran |
| --- | --- | --- | --- |
| linoleic acid | 59.34% | 50.3% | 49.2% |
| oleic acid | 23.58% | 25.0% | 23.7% |
| palmitic acid | 11.9% | 17.2% | 18.4% |

The following results (on a dry-weight basis) were obtained for Tunisian and Iranian *Nigella sativa*, respectively: protein 26.7% and 22.6%, oil 28.48% and 40.35%, ash 4.86% and 4.41%, and total carbohydrates 40.0% and 32.7%. The major unsaturated fatty acids were linoleic acid (50.3%, 49.2%), followed by oleic acid (25.0%, 23.7%), while the main saturated fatty acid was palmitic acid (17.2%, 18.4%) for *Nigella sativa* grown in Tunisia and Iran, respectively. Myristic, myristoleic, palmitoleic, margaric, margaroleic, stearic, linolenic, arachidic, eicosenoic, behenic and lignoceric acids were also detected (Cheikh-Rouhou S, Besbes S, Hentati B, Blecker C, Deroanne C, Attia H. *Nigella sativa* L.: Chemical composition and physicochemical characteristics of lipid fraction. Food Chemistry 2007; 101(2):673-681, incorporated herein by reference in its entirety).

In preferred embodiments, *Nigella sativa* grown in Saudi Arabia are used in the method disclosed herein. Proximate analysis of black cumin seeds showed a composition of 20.85 wt % protein, 38.20 wt % fat, 4.64 wt % moisture, 4.37 wt % ash, 7.94 wt % crude fibre and 31.94 wt % total carbohydrates, based on a total weight of *Nigella sativa* seeds (Al-Jassir M. Chemical composition and microflora of black cumin (*Nigella sativa* L.) seeds growing in Saudi Arabia. Food chemistry. 1992; 45(4):239-42, incorporated herein by reference in its entirety). Potassium, phosphorus, sodium and iron were the predominant elements present. Zinc, calcium, magnesium, manganese and copper were found at lower levels. However, lead, cadmium and arsenic were not detected in the seeds. Linoleic and oleic acids were the major unsaturated fatty acids while palmitic acid was the main saturated one. Glutamic acid, arginine and aspartic acid were the main amino acids present while cystine and methionine were the minor amino acids. These results indicate the high nutritional potential of Saudi black cumin seeds especially as a source of protein and fat. Thus, *Nigella sativa* from Saudi Arabia may be preferred over other sources because the plant contains high amounts of linoleic acid. For example, an amount of linoleic acid in the fixed oil derived from *Nigella sativa* from Saudi Arabia may be 5-30 percentage points, 8-20 percentage points, or 10-15 percentage points higher than corresponding amounts in the fixed oil derived from *Nigella sativa* from other parts of the world.

The essential oil of *Nigella sativa* includes thymoquinone (10-70%, 20-60%, or 27-57%), p-cymene (1-20%, 5-17%, or 7.1-15.5%), carvacrol (1-20%, 3-14%, or 5.8-11.6%), trans-anethole (0.1-5%, 0.2-4%, or 0.25-2.3%), p-terpineol (1-10%, 1.5-8%, or 2-6.6%), longifoline (0.5-10%, or 1-8%), each based on a total volume of the essential oil. The essential oil also contains nigellone, thymohydroquinone, thymol, α-pinene, β-pinene, d-limonene, d-citronellol, and 4-terpineol. Thymoquinone readily dimerizes to form dithymoquinone and in the context of the present disclosure, thymoquinone also refers to the dimer dithymoquinone.

*Nigella sativa* and its active component (thymoquinone) demonstrated multiple therapeutic effects in several studies. *Nigella sativa* is anti-inflammatory, antioxidant, antibacterial, hypoglycemic, and antilipidemic (Hajhashemi V, Ghannadi A, Jafarabadi H. Black cumin seed essential oil, as a potent analgesic and anti-inflammatory drug. Phytother Res. 2004 Mar., 18(3):195-9. PubMed PMID: 15103664; Mansour M A, Nagi M N, El-Khatib A S, Al-Bekairi A M. Effects of thymoquinone on antioxidant enzyme activities, lipid peroxidation and DT-diaphorase in different tissues of mice: a possible mechanism of action. Cell Biochem Funct. 2002 Jun.; 20(2):143-51. PubMed PMID: 11979510; Hawsawi Z A, Ali B A, Bamosa A O. Effect of *Nigella sativa* (black seed) and thymoquinone on blood glucose in albino rats. Ann Saudi Med. 2001 2001 May-Jul.; 21(3-4):242-4. PubMed PMID: 17264566; and Ali B H, Blunden G. Pharmacological and toxicological properties of *Nigella sativa*. Phytother Res. 2003 Apr.; 17(4):299-305. PubMed PMID: 12722128, each incorporated herein by reference in their entirety). Thymoquinone was isolated and recognized as an important and active constituent of both the essential and fixed oils (Salma Cheikh-Rouhoua, Souhail Besbesa, Basma Hentatib, Christophe Bleckerc, Claude Deroannec, Hamadi Attiaa. *Nigella sativa* L: Chemical composition and physicochemical characteristics of lipid fraction. 2007. p. 673-81, incorporated herein by reference in its entirety).

*Nigella sativa* was found to have antihypertensive effects. Two previous studies reported antihypertensive effect on *Nigella sativa* on human and animals (Dehkordi F R, Kamkhah A F. Antihypertensive effect of *Nigella sativa* seed extract in patients with mild hypertension. Fundam Clin Pharmacol. 2008 Aug.; 22(4):447-52. PubMed PMID: 18705755; and Khattab M M, Nagi M N. Thymoquinone supplementation attenuates hypertension and renal damage in nitric oxide deficient hypertensive rats. Phytother Res. 2007 May; 21(5):410-4. PubMed PMID: 17236176, each incorporated herein by reference in their entirety). Cardiac adaptation for long term administration of *Nigella sativa* was also demonstrated. In a study performed by El Bahai et al. long-term administration of *Nigella sativa* for two months for adult Wistar rats, lead to increases in the peak force of contraction, myocardial flow rate and the rate of tension development (El-Bahai M N, Al-Hariri M T, Yar T, Bamosa A O. Cardiac inotropic and hypertrophic effects of *Nigella sativa* supplementation in rats. Int J Cardiol. 2009

January; 131(3):e115-7. PubMed PMID: 17931720, incorporated herein by reference in its entirety). Another study performed by the same group, showed structural remodeling of the myocardium, including myocardial hypertrophy manifested by increased heart weight/body weight (HW/BW), left ventricular weight/body weight (LVW/BW), and increased diameters of cardiomyocytes when *Nigella sativa* was fed to rats which were exercise-trained (Al-Asoom L I, Al-Shaikh B A, Bamosa A O, El-Bahai M N. Effect of *Nigella sativa* supplementation to exercise training in a novel model of physiological cardiac hypertrophy. Cardiovasc Toxicol. 2014 Sep.; 14(3):243-50. PubMed PMID: 24497112, incorporated herein by reference in its entirety). The histological and electrophysiological characteristics of hypertrophied hearts induced by *Nigella sativa* in combination with exercise were compared to exercise-induced cardiac hypertrophy, and multiple similarities were found (Al-Asoom L I, Al-Shaikh B A, Bamosa A O, El-Bahai M N. Comparison of *Nigella sativa*- and exercise-induced models of cardiac hypertrophy: structural and electrophysiological features. Cardiovasc Toxicol. 2014 Sep.; 14(3):208-13. PubMed PMID: 24448711, incorporated herein by reference in its entirety). Furthermore, Ansam et al. reported a protective effect of *Nigella sativa* against ischemia reperfusion insult in rat hearts when the animals fed *Nigella sativa* for three months (Seif A A. *Nigella sativa* attenuates myocardial ischemic reperfusion injury in rats. J Physiol Biochem. 2013 December; 69(4):937-44. PubMed PMID: 23846789, incorporated herein by reference in its entirety).

However, none of the literature reported coronary angiogenesis occurring as a result of administering *Nigella sativa* or that *Nigella sativa* may be useful for treating ischemic heart disease. In addition, the method disclosed herein effects coronary angiogenesis without causing cardiac hypertrophy, which is unexpected. In the present disclosure, the angiogenic and therapeutic effects of *Nigella sativa* may be at least partially attributed to thymoquinone.

An essential oil, a plant extract, or a part of *Nigella sativa* plant may be administered to the subject. Essential oils are aromatic oily liquids obtained from plant materials (e.g., the whole plant, flowers, buds, seeds, leaves, twigs, stem, bark, fruits, roots, and combinations thereof). Preferably, the essential oil is extracted from *Nigella sativa* seeds. Essential oils are a rich source of biologically active compounds (e.g., hydrocarbons, such as monoterpenes and sesquiterpenes; and oxygenated compounds, such as monoterpenoids, sesquiterpenoids, esters, ethers, aldehydes, ketones, and oxides).

Plant extracts, as defined herein, are not "essential oils" as noted above. The plant extract may be obtained from any of the plant parts including the leaves, pulp, seeds, stems, fruit and fruit seeds, as well as the whole plant. The plant extract comprises phytochemicals and/or metabolites that include, without limitation, alkaloids, flavonoids, saponins, carbohydrates, polysaccharides, terpenoids (e.g., monoterpenoids and sesquiterpenoids), steroids, sterols, phenols, tannins, anthraquinones, anthocyanins, amino acids, proteins, and vitamins.

In some embodiments, a part of the *Nigella sativa* plant (e.g., flowers, buds, seeds, leaves, twigs, stem, bark, fruits, roots, and combinations thereof) is administered to the subject. The plant part(s) of interest may be collected and then washed thoroughly, preferably twice/thrice with water, to remove both epiphytes and necrotic plants; preferably followed by washing with water to remove associated debris if any. In some embodiments, tap water, distilled water, doubly distilled water, deionized water, deionized distilled water, or combinations thereof may be used to wash the plant part(s) of interest. The water may be sterile. In one embodiment, the water may have a conductivity of less than 10 $\mu S \cdot cm^{-1}$, less than 5 $\mu S \cdot cm^{-1}$, or less than 1 $\mu S \cdot cm^{-1}$ at 20-30° C.; and/or a resistivity greater than 0.1 $M\Omega \cdot cm$, greater than 1 $M\Omega \cdot cm$, greater than 5 $M\Omega \cdot cm$, or greater than 10 $M\Omega \cdot cm$ at 20-30° C.; and/or a total solid concentration less than 5 mg/kg, less than 1 mg/kg, or less than 0.5 mg/kg; and/or a total organic carbon concentration less than 1000 µg/L, less than 200 µg/L, or less than 50 µg/L. The clean and fresh plant parts may be sun-dried or dried in the shade for 5-25 days, or preferably 7-20 days, or more preferably 10-15 days, and then finely cut/chopped, or preferably ground/powdered/pulverized using, for example, a domestic blender. In preferred embodiments, the clean *Nigella sativa* seeds may be ground with a flax mill, a spice mill, a coffee grinder, a food processor, a pepper mill, or a mortar and pestle. At least 80%, at least 85%, at least 90%, at least 95%, at least 99% of the ground *Nigella sativa* seeds may pass through a mesh size larger than 20, larger than 100, or larger than 200.

The essential oil of *Nigella sativa* may be obtained by expression, fermentation, distillation, steam distillation, pressing, organic extraction, supercritical $CO_2$ extraction, or additional extraction methods known to those familiar in the art. For example, the essential oil may be obtained by extracting fresh/dried/ground plant part(s) of interest with supercritical $CO_2$ at a pressure of 140-300 bar, 180-250 bar, or 200-220 bar, at 50-80° C., or 55-70° C., for 30-240 minutes, 60-180 minutes, or 100-150 minutes.

The *Nigella sativa* plant may be at any growth stage, e.g. at a flowering stage when the flower and/or one or more non-flower parts (e.g. leaf, stem, and root) may be used to make the essential oil and/or the aqueous extract, or alternatively, at a non-flowering stage, when one or more non-flower parts may be used to make the essential oil and/or the aqueous extract.

The aqueous extract may be prepared as follows. The fresh/dried/ground plant part(s) may be mixed with water (e.g., deionized distilled water) in an amount of 0.01-5 g/ml, 0.05-3 g/ml, 0.1-2 g/ml or 0.2-1 g/ml of water. The resulting mixture may be heated at a temperature of 60-100° C., 70-90° C., or 75-85° C. for 1-30 minutes, preferably 5-25 minutes, or more preferably 10-20 minutes. In some embodiments, the hot water percolation method is used. The aqueous extract may be administered as it is to the subject. In some embodiments, the resulting infusion is filtered until no insoluble material appears in the aqueous extract prior to the administering.

In some embodiments, the ground plant part(s) or composition is freshly prepared prior to every administering. The ground plant part(s) or composition may be administered 0.1-120 s, 1-80 s, or 10-60 s after preparation. In some embodiments, the ground plant part(s) or composition is administered 2-15 minutes, 5-12 minutes, or 8-10 minutes after preparation.

In most embodiments, the *Nigella sativa* is formulated in a composition. As used herein, a "composition" refers to a mixture of the *Nigella sativa* with other chemical components, such as pharmaceutically acceptable carriers and excipients (either inert or active), making the composition especially suitable for therapeutic use in vivo. One purpose of a composition is to facilitate administration of the *Nigella sativa* to the subject. The composition may contain 1-50 wt % *Nigella sativa*, 3-40 wt %, 6-20 wt %, or 8-15 wt %, based on a total weight of the composition. In most embodiments, the composition consists essentially of *Nigella sativa* and water. Ingredients which do not affect angiogenesis may be included in such compositions.

As used herein, the phrase "pharmaceutically acceptable" refers to the composition is within the scope of sound medical judgment, suitable for use in contact with the tissues of human beings and animals without excessive toxicity, irritation, allergic response, or other problem or complication, commensurate with a reasonable benefit/risk ratio.

As used herein, a "pharmaceutically acceptable carrier" refers to a carrier or diluent that does not cause significant irritation to an organism, does not abrogate the biological activity and properties of the administered *Nigella sativa*, and/or does not interact in a deleterious manner with the other components of the composition in which it is contained. The term "carrier" encompasses any excipient, binder, diluent, filler, salt (e.g., sodium chloride), buffer (e.g., phosphate buffered saline), solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of *Nigella sativa*. Examples, without limitation, of excipients include calcium carbonate, calcium phosphate, various sugars and types of starch, cellulose derivatives, gelatin, vegetable oils, and polyethylene glycols.

As used herein, the terms "therapies" and "therapy" can refer to any method or composition that can be used in the treatment and/or management of the disease or one or more symptoms thereof. In some embodiments, the method disclosed herein may be administered to the subject before and/or after surgeries such as angioplasty (e.g., percutaneous coronary intervention, also known as coronary angioplasty), bypass grafting, and carotid endarterectomy. For example, the subject may be administered with *Nigella sativa* for up to 8 weeks, 6 weeks, or 2 weeks before the surgery.

In some embodiments, the method disclosed herein is used in conjunction with prescribed medicine for high cholesterol and/or high blood pressure (e.g., statins, bile acid sequestrants, cholesterol absorption inhibitors, fibrates, niacin, thiazide diuretics, omega-3 fatty acid supplements, beta blockers, angiotensin-converting enzyme (ACE) inhibitors, angiotensin II receptor blockers (ARBs), calcium channel blockers, alpha blockers, alpha-beta blockers, central-acting agents, vasodilators, aldosterone antagonists, and renin inhibitors). The administration of the prescribed medicine may be concurrent with *Nigella sativa* or staggered.

In some embodiments, the method includes administering a second plant to the subject. The amount of the second plant may range from 1-100 wt %, 3-70 wt %, 6-50 wt %, or 10-30 wt % relative to the weight of *Nigella sativa* of the first effective amount. Preferably, the second plant also contains thymoquinone. Examples of second plants include, without limitation, *Monarda didyma, Monarda media, Monarda menthifolia, Thymus pulegioides, Thymus serpyllum, Thymus vulgaris, Satureja hortensis, Satureja montana, Eupatorium cannabinum*, and *Juniperus communis*. An essential oil, a plant extract, or a part (fresh/dried/ground) of the second plant may be administered. The administration of the second plant may be concurrent with *Nigella sativa* or staggered.

A time interval between the administration of *Nigella sativa* and the administration of the prescribed medicine and/or the second plant may be about 1-5 minutes, 1-30 minutes, 30 minutes to 60 minutes, 1 hour, 1-2 hours, or 2-6 hours.

The terms "administer", "administering", "administration", and the like, as used herein, refer to the methods that may be used to enable delivery of the *Nigella sativa* and/or the composition to the desired site of biological action. Routes or modes of administration are as set forth herein. These methods include, but are not limited to, oral routes or via a gastrostomy tube. Those of ordinary skill in the art are familiar with administration techniques that can be employed with the composition and methods described herein. In preferred embodiments, the *Nigella sativa* and/or the composition described herein are administered orally.

Solid dosage forms for oral administration can include capsules, tablets, pills, powders, and granules. In such solid dosage forms, *Nigella sativa* is ordinarily combined with one or more adjuvants appropriate to the indicated route of administration. *Nigella sativa* can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of pulverized parts of *Nigella sativa* in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavoring, and perfuming ingredients.

Emulsifiers may be added for stability of the final product. Examples of suitable emulsifiers include, but are not limited to, lecithin (e.g., from egg or soy), or mono- and diglycerides. Other emulsifiers are readily apparent to the skilled artisan and selection of suitable emulsifier(s) will depend, in part, upon the formulation and final product.

In addition to the carbohydrates described herein, the composition can contain natural or artificial sweeteners, e.g., sucrose, fructose, cyclamates, asparagine, sucralose, aspartame, and acesulfame K.

For therapeutic purposes, formulations for administering via the gastrostomy tube can be in the form of aqueous or non-aqueous isotonic sterile solutions or suspensions. These solutions and suspensions can be prepared from sterile *Nigella sativa* powder or granules and one or more of the carriers or diluents mentioned for use in the formulations for oral administration. *Nigella sativa* can be mixed with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. The sterile solution/suspension may be prepared in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of sterile solution/suspension. Dimethyl acetamide, surfactants including ionic and non-ionic detergents, polyethylene glycols can be used. Mixtures of solvents and wetting ingredients such as those discussed above are also useful.

In other embodiments, *Nigella sativa* is provided as dietary supplement in capsule or tablet form. *Nigella sativa* can be formulated into a food or drink, and provided, for example, as a snack bar, a cereal, a drink, or in any other easily ingested form. Flavors, coloring agents, spices, nuts and the like can be incorporated into the product. Flavorings can be in the form of flavored extracts, essential oils, chocolate flavorings (e.g., non-caffeinated cocoa or chocolate, chocolate substitutes such as carob), peanut butter flavoring, cookie crumbs, crisp rice, vanilla or any commercially available flavoring. Flavorings can be protected with mixed tocopherols. Examples of useful flavorings include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or essential oils, such as balm oil, bay oil, bergamot oil, cedar wood oil, cherry oil, walnut oil, cinnamon oil, clove oil, or peppermint oil; peanut butter, chocolate flavoring, vanilla cookie crumb, butterscotch or toffee. In a preferred embodiment, the dietary supplement contains berry or other fruit flavor. The food compositions may further be coated, for example with a yogurt coating if it is as a bar.

Preservatives may also be added to the composition to extend product shelf life. Preferably, preservatives such as potassium sorbate, sodium sorbate, potassium benzoate, and sodium benzoate are used.

As used herein, the term "beverage" means a consumer ready product comprising any liquid intended for human or animal consumption. Exemplary types of beverages include, but are not limited to, berries and small fruit juices, smoothies, citrus fruit juices, dairy products (i.e. milks, yogurts, and soy beverages), grape juices, syrups, wines, beers, teas, coffees, cocoas/chocolates, tomato juices, and the like. The beverage contain *Nigella sativa* and may contain other ingredients such as vitamins, natural and artificial flavors, electrolytes, dietary fiber, calcium, iron, zinc, calcium disodium EDTA, citric acid, $CO_2$, the second plant, or any other desired ingredient.

In one embodiment, the beverage is a tea, an aromatic beverage commonly prepared by pouring hot or boiling water over a plant or plant parts. For example, the fresh/dried/ground plant part(s) may be mixed with boiled water (the temperature of the water may be 80-100° C., 90-100° C., preferably 95-100° C.) and left to steep for 1-5 minutes, 2-4 minutes, or about 3 minutes. In certain embodiments, the beverage of the present disclosure may further comprise one or more plants, including herbal tea plants. Exemplary plants include, but are not limited to, anise (seeds or leaves), asiatic penny-wort leaf, artichoke, bee balm, boldo, burdock, caraway, catnip, chamomile, che dang (*ilex causue* leaves), chinese knot-weed, chrysanthemum, cinnamon, cocoa, coffee leaves and coffee cherry, cerasse, citrus peel (including bergamot, lemon and orange peels), dandelion coffee, dill, echinacea, elderberry, european mistletoe (*viscum album*), essiac, fennel, gentian, ginger root, ginseng, goji, hawthorn, hibiscus, ho yan hor herbal, honeybush, horehound, houttuynia, *hydrangea* (*hydrangea serrata* amacha), jiaogulan, kapor, kava root, kratom, kuzuyu, labrador, lapacho (also known as taheebo), lemon balm, lemon and ginger, lemon grass, luo han guo, licorice root, lime blossom, mint, mountain, neem leaf, nettle leaf, new jersey, noni, oksusu cha, pennyroyal leaf, pine, qishr, red clover, red raspberry leaf, roasted barley, roasted wheat, rooibos (red bush), rose hip, roselle petals (species of hibiscus; aka bissap, dah, etc.), rosemary, sagebrush, california sagebrush, sage, sakurayu, salvia, scorched rice, skullcap, sobacha, spicebush (*lindera benzoin*), spruce, staghorn sumac fruit, stevia, St. John's wort, thyme, tulsi, holy basil, *uncaria tomentosa* (commonly known as cat's claw), valerian, verbena (vervains), vetiver, wax gourd, wong lo kat, woodruff, yarrow, and the like and mixtures thereof.

The first aspect of the disclosure relates to a method for effecting angiogenesis and optionally treating ischemia. The method comprises administering a first effective amount of *Nigella sativa* to a subject in need thereof.

The terms "effective amount", "therapeutically effective amount", or "pharmaceutically effective amount" refer to that amount of the *Nigella sativa* being administered which will relieve to some extent one or more of the symptoms of the disease being treated. The result can be reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. The dosage and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly.

The first effective amount may be in a range of 0.1-1 g/kg body weight of the subject, 0.3-0.95 g/kg, 0.6-0.9 g/kg, or 0.7-0.85 g/kg. The first effective amount of *Nigella sativa* may be administered 1-3 times a day, 1-2 times/day, or preferably once a day. The first effective amount of *Nigella sativa* may be administered 2-6 days, 3-6 days, or 4-6 days per week for a period of 4-52 weeks, 5-40 weeks, 6-30 weeks, or preferably 7-10 weeks. In preferred embodiments, the first effective amount of *Nigella sativa* is administered for 4-6 consecutive days per week. Accordingly, a time lapse of 1-3 days is present between each administering. In some embodiments, the first effective amount is administered once a week and may still effect coronary angiogenesis and optionally treat ischemic heart disease.

In some preferred embodiments, this cycling method effects coronary angiogenesis but does not lead to cardiac hypertrophy in the subject. As used herein, the term "cardiac hypertrophy" refers to thickening of the heart muscle which results in a decrease in size of the chamber of the heart, including the left and right ventricles. Cardiac hypertrophy may be determined with electrocardiography, ultrasound, or computed tomography. In some embodiments, cardiac hypertrophy is determined from the levels of PECAM-1 which is described hereinafter. Alternatively, the presence of cardiac hypertrophy may be determined from the weight of the heart, the weight of each of the left and right ventricles, the ratio between the heart weight and the subject's weight, the ratio between the weight of the left/right ventricle and the subject's weight, and an average diameter of cardiomyocytes. An average diameter of cardiomyocytes in a hypertrophic (i.e., enlarged) heart may be at least 10%, 20%, 40%, 60%, or 80% larger than an average diameter of cardiomyocytes in a normal heart. Normal cardiomyocytes may have an average diameter in a range of 10-25 µm, 12-22 µm, or 15-20 µm. As used herein, the term "diameter" refers to the greatest possible distance measured from a first point on a cross-section of the cardiomyocyte through the center of the cross-section to a second point directly across from the first point. An average weight of a normal adult human heart may be 88-235 g, 100-200 g, or 160-180 g (R. M. Fulton, E. C. Hutchinson, And A. Morgan Jones, Ventricular Weight In Cardiac Hypertrophy, British Heart Journal, 1952, 14: 413-420, incorporated herein by reference in its entirety). An average weight of a normal right ventricle may be 23-68 g, 30-60 g, or 40-50 g. An average weight of a normal left ventricle may be 48-123 g, 50-110 g, or 80-90 g. An average weight of a heart with cardiac hypertrophy may weigh at least 20%, at least 50%, or at least 80% heavier than a normal heart, for example, 173-606 g, 200-500 g, or 220-400 g. An average weight of a hypertrophic right ventricle may weigh at least 20%, at least 50%, or at least 70% heavier than a normal right ventricle, for example, 55-178 g, 60-150 g, or 75-110 g. An average weight of a hypertrophic left ventricle may weigh at least 50%, at least 80%, or at least 90% heavier than a normal left ventricle, for example, 121-346 g, 150-250 g, or 170-220 g. In preferred embodiments, the weight of the subject's heart falls within the weight range for a normal heart, or the weight of the subject's left or right ventricle falls within the weight range for a normal left or right ventricle, respectively, before and after the administration of Nigella sativa.

In most embodiments, the method further comprises measuring a concentration of a biomarker and/or detecting a mutation in a biomarker before and/or after the Nigella sativa is administered. As used herein, the term "biomarker" refers to a characteristic that is objectively measured and evaluated as an indicator of normal biological processes, pathogenic processes or pharmacological responses to a therapeutic intervention. Exemplary biomarkers related to angiogenesis and/or ischemia include, without limitation, angiogenic proteins (including several growth factors) such as fibroblast growth factor (FGF), vascular endothelial growth factor (VEGF), vascular endothelial growth factor receptor (VEGFR), neuropilin-1 (NRP-1), angiopoietin 1 (Ang1), angiopoietin 2 (Ang2), platelet-derived growth factor (PDGF), platelet-derived growth factor receptor (PDGFR), transforming growth factor beta (TGF-β), transforming growth factor beta receptor, endoglin, chemokine ligand 2 (CCL2), integrins $\alpha_v\beta_3$, $\alpha_v\beta_5$ and $\alpha_5\beta_1$, vascular endothelial cadherin, platelet endothelial cell adhesion molecule (PECAM-1), ephrin, plasminogen activators, plasminogen activator inhibitor-1, nitric oxide synthase 3 (eNOS), cyclooxygenase-2 (COX-2), AC133, DNA-binding protein inhibitor ID-1, DNA-binding protein inhibitor ID-3, and class 3 semaphorins; myeloperoxidase (MPO); cardiac troponin T (cTnT) and troponin I (cTnI); C-reactive protein (CRP); and other inflammatory biomarkers such as cytokines (interleukin (IL)-1, IL-6, IL-8, monocyte chemoattractant protein-1 (MCP-1)), soluble CD40 ligand, serum amyloid A (SAA), selectins (E-selectin, P-selectin), matrix metalloproteinases (MMPs), cellular adhesion molecules (intercellular adhesion molecule 1 (ICAM-1), and vascular adhesion molecule 1 (VCAM-1)); placental growth factor (PlGF); A2 phospholipases; low-density lipoprotein (LDL) receptor gene; APOE gene; lecithin-cholesterol acyltransferase gene; and ATP binding cassette transporter (ABCA1) gene.

VEGF is a growth factor that induces the sprouting of the capillaries. It does so by dissolving the basement membrane of the existing capillaries, and then stimulating the proliferation and migration of endothelial cells (Zheng W, Seftor E A, Meininger C J, Hendrix M J, Tomanek R J. Mechanisms of coronary angiogenesis in response to stretch: role of VEGF and TGF-beta. Am J Physiol Heart Circ Physiol. 2001 February; 280(2):H909-17. PubMed PMID: 11158993, incorporated herein by reference in its entirety). VEGF interacts with the endothelial cell adhesion molecules during the process of endothelial growth and proliferation (Kolmakova A, Rajesh M, Zang D, Pili R, Chatterjee S. VEGF recruits lactosylceramide to induce endothelial cell adhesion molecule expression and angiogenesis in vitro and in vivo. Glycoconj J. 2009 Jul.; 26(5):547-58. PubMed PMID: 19219548, incorporated herein by reference in its entirety). In one study, rats that exercised for four weeks were found to have upregulation of VEGF, accompanied simultaneously with capillary sprouting and capillary angiogenesis (Al-Asoom L I, Al-Shaikh B A, Bamosa A O, El-Bahai M N. Comparison of Nigella sativa and exercise-induced models of cardiac hypertrophy: structural and electrophysiological features. Cardiovasc Toxicol. 2014 Sep.; 14(3):208-13, incorporated herein by reference in its entirety). Induction of VEGF production in an endothelial cell culture has been found to promote cell division and cell proliferation (Peng Y Z, Zheng K, Yang P, Wang Y, Li R J, Li L, et al. Shock wave treatment enhances endothelial proliferation via autocrine vascular endothelial growth factor. Genet Mol Res. 2015; 14(4):19203-10. PubMed PMID: 26782573, incorporated herein by reference in its entirety). Nurro et al. showed that the administration of VEGF genes into porcine myocardium induced angiogenesis and increased the microvascular bed about 1.8 fold (Nurro J, Halonen P J, Kuivanen A, Tarkia M, Saraste A, Honkonen K, et al. AdVEGF-B186 and AdVEGF-DANAC induce angiogenesis and increase perfusion in porcine myocardium. Heart. 2016 November; 102 (21):1716-20. PubMed PMID: 27173504, incorporated herein by reference in its entirety).

The process of angiogenesis is also governed by antiangiogenic factors. VWF is a glycoprotein that is synthesised in the endothelial cells, and it is known for its essential haemostatic effect. It stimulates the adhesion and aggregation of platelets in injured tissue, and it acts as a carrier of coagulation factor VIII (Randi A M, Laffan M A, Starke R D. Von Willebrand factor, angiodysplasia and angiogenesis. Mediterr J Hematol Infect Dis. 2013; 5(1):e2013060. PubMed PMID: 24106610. Pubmed Central PMCID: PMC3787682, incorporated herein by reference in its entirety). VWF plays a role in the regulation of angiogenesis, limits the release of angiogenic factors, such as VEGF, and stabilises the capillary bed (Starke R D, Ferraro F, Paschalaki K E, Dryden N H, McKinnon T A, Sutton R E, et al. Endothelial von Willebrand factor regulates angiogenesis. Blood. 2011 January; 117(3):1071-80. PubMed PMID: 21048155. Pubmed Central PMCID: PMC3035068, incorporated herein by reference in its entirety). A deficiency in VWF results in abnormal growth of vessels in angiodysplasia (Bauditz J, Lochs H. Angiogenesis and vascular malformations: antiangiogenic drugs for treatment of gastrointestinal bleeding. World J Gastroenterol. 2007 Dec.; 13(45): 5979-84. PubMed PMID: 18023086. Pubmed Central PMCID: PMC4250877, incorporated herein by reference in its entirety). Inhibition of the synthesis and release of VWF by interfering with its genetic expression in mice leads to enhanced angiogenesis, increased VEGF receptor-2 dependent proliferation and migration of endothelial cells.

Nitric oxide (NO) is a multifunctional cellular signalling molecule, known for its vasodilation action. Recently, evidence has shown that NO plays a role as a mediator of angiogenesis. NO is released from the endothelial cells under the influence of VEGF. VEGF upregulates and activates nitric oxide synthase (NOS) in endothelial cells (Cooke J P, Losordo D W. Nitric oxide and angiogenesis. Circulation. 2002 May; 105(18):2133-5. PubMed PMID: 11994243, incorporated herein by reference in its entirety). Increased expression of NOS was demonstrated in the hind-limbs of mice after three weeks of wheel running (Schirmer S H, Millenaar D N, Werner C, Schuh L, Degen A, Bettink S I, et al. Exercise promotes collateral artery growth mediated by monocytic nitric oxide. Arterioscler Thromb Vasc Biol. 2015 August; 35(8):1862-71. PubMed PMID: 26088573, incorporated herein by reference in its entirety). Overexpression of both endothelial and inducible NOS was also demonstrated in the heart after training in both mice and humans. Ischemia might be a crucial trigger for the release and synthesis of inducible NOS (iNOS, also known as NOS-2), and its upregulation after exercise training depends on the degree of ischemia induced by the training intensity (Kleindienst A, Battault S, Belaidi E, Tanguy S, Rosselin M, Boulghobra D, et al. Exercise does not activate the β3 adrenergic receptor-eNOS pathway, but reduces inducible NOS expression to protect the heart of obese diabetic mice. Basic Res Cardiol. 2016 July; 111(4): 40. PubMed PMID: 27164904, incorporated herein by reference in its entirety). *Nigella sativa* is known to be an anti-inflammatory and antioxidant mediator and it might not culminate in overexpression of NOS-2.

PECAM-1 is the platelet-endothelial adhesion molecule known as CD31 (Feng D, Nagy J A, Pyne K, Dvorak H F, Dvorak A M. Ultrastructural localization of platelet endothelial cell adhesion molecule (PECAM-1, CD31) in vascular endothelium. J Histochem Cytochem. 2004 January; 52(1): 87-101. PubMed PMID: 14688220, incorporated herein by reference in its entirety). The interaction of PECAM-1 with growth factors is essential for angiogenesis (DeLisser H M, Christofidou-Solomidou M, Strieter R M, Burdick M D, Robinson C S, Wexler R S, et al. Involvement of endothelial PECAM-1/CD31 in angiogenesis. Am J Pathol. 1997 September; 151(3):671-7. PubMed PMID: 9284815. Pubmed Central PMCID: PMC1857836, incorporated herein by reference in its entirety). Some studies have used PECAM-1 to estimate capillary density. In a recent study, diabetic rats were exposed to testosterone treatment and exercise to investigate the effect on these two interventions on neoangiogenesis (Nurro J, Halonen P J, Kuivanen A, Tarkia M, Saraste A, Honkonen K, et al. AdVEGF-B186 and AdVEGF-DANAC induce angiogenesis and increase perfusion in porcine myocardium. Heart. 2016 November; 102 (21):1716-20, incorporated herein by reference in its entirety). That study demonstrated more PECAM-1 antibody staining after both treatment modalities were administered (Chodari L, Mohammadi M, Ghorbanzadeh V, Dariushnejad H, Mohaddes G. Testosterone and Voluntary Exercise Promote Angiogenesis in Hearts of Rats with Diabetes by Enhancing Expression of VEGF-A and SDF-1a. Can J Diabetes. 2016 July PubMed PMID: 27444229, incorporated herein by reference in its entirety). Cardiac hypertrophy is associated with an augmented blood vessel density (Marc Thiriet, Diseases of the Cardiac Pump, Springer, 2015). As such high PECAM-1 levels may be indicative of cardiac hypertrophy.

Cardiac troponins may be elevated in acute coronary syndromes and are used to assess ischemic heart diseases.

Myeloperoxidase (MPO) is involved in the inflammatory process that precedes the onset of symptomatic coronary artery disease (Meuwese M C, Stroes E S, Hazen S L et al.: Serum myeloperoxidase levels are associated with the future risk of coronary artery disease in apparently healthy individuals: the EPIC-Norfolk Prospective Population Study. J. Am. Coll. Cardiol. 50, 159-165 (2007), incorporated herein by reference in its entirety). Elevated levels of myeloperoxidase may predict future risk of coronary artery disease in apparently healthy individuals who do not show the symptoms.

The mutation in the biomarker may be detected with a polymerase chain reaction (PCR) assay, DNA microarray, multiplex ligation-dependent probe amplification (MLPA), single strand conformational polymorphism (SSCP), denaturing gradient gel electrophoresis (DGGE), heteroduplex analysis, and restriction fragment length polymorphism (RFLP). The procedures to detect the mutation are well-known to those of ordinary skill in the art.

The concentration of the biomarker may be measured with an assay, for example an antibody-based method (e.g., an ELISA). As used herein, the term "antibody-based method" refers to any method with the use of an antibody including, but not limited to, enzyme-linked immunosorbent assay (ELISA), Western blotting, immunoprecipitation (IP), enzyme linked immunospot (ELISPOT), immunostaining, immunohistology (immunohistochemistry), immunocytochemistry, affinity chromatography, and the like.

In preferred embodiments, immunohistology is used to detect and quantify the biomarkers in a sample. The biomarker may be detected with a direct or indirect method. The direct method is a one-step staining method and involves a labelled antibody (e.g. FITC-conjugated antibody) reacting directly with the biomarker in the sample. The indirect method involves an unlabelled primary antibody that binds to the biomarker in the sample and a labelled secondary antibody that reacts with the primary antibody. In some embodiments, after the biomarker has reacted with the antibody, a dye is applied to provide additional contrast. Exemplary dyes include, without limitation, hematoxylin, Hoechst stain, and DAPI.

The stained areas may be visualized by a confocal microscope or an optical microscope. Soft copies of the micrographs may be obtained with the microscopes or by digitizing images from hard copies of micrographs. A software, such as ImageJ or a proprietary software provided by the microscope vendor, may be used to analyze/quantify the stained areas. The stained areas in each micrograph are expressed as a percentage of the total area of each micrograph. This percentage is proportional to the amount of the biomarkers present in the sample.

In accordance with the method of quantification described in the preceding paragraph, an amount of VEGF before administering the first effective amount or in a subject who is not treated with *Nigella sativa* may be in a range of 0.8-2.4%, 1-2%, or 1.5-1.6%. An amount of VEGF after administering the first effective amount may be in a range of 1.2-4%, 1.5-3.5%, 2-3%, or 2.5-2.7%.

An amount of VWF before administering the first effective amount or in a subject who is not treated with *Nigella sativa* may be in a range of 0.6-4.1%, 2-3%, or 2.3-2.4%. An amount of VWF after administering the first effective amount may be in a range of 0.7-2.4%, 0.9-2%, 1.2-1.8%, or 1.4-1.6%.

An amount of PECAM-1 before administering the first effective amount or in a subject who is not treated with *Nigella sativa* may be in a range of 0.02-2.36%, 0.5-2%, 1-1.5%, or 1.1-1.3%. In embodiments where the method effects coronary angiogenesis without causing cardiac hypertrophy, the amount of PECAM-1 is substantially the same (e.g., deviates less than 15%, 10%, 5%, 3%, 2%, or 1%) as the amount of PECAM-1 before administering the first effective amount. Elevated levels of PECAM-1 may be in a range of 1-2.6%, 1.3-2%, or 1.6-1.9. In some embodiments where the sample contains heart cells, elevated levels of PECAM-1 indicate cardiac hypertrophy.

In preferred embodiments, an amount of NOS-2 before and after administering the first effective amount may be in a range of 0.06-2.44%, 0.5-2%, 1-1.5%, or 1.1-1.3%.

In some embodiments, an ELISA is used. The term "ELISA" refers to a method of detecting the presence and quantify of a biomarker in a sample. There are several variants of ELISA, including, but not limited to, sandwich ELISA, competitive ELISA, indirect ELISA, ELISA reverse, and the like. The ELISA assay may be a singleplex assay or a multiplex assay, which refers to a type of assay that simultaneously measures multiple analytes in a single run/cycle of the assay. Preferably, a sandwich ELISA is used.

The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

The term "sample" includes any biological sample taken from the subject including cells (e.g., cardiac muscle cells, brain cells, kidney cells, and intestine cells), a tissue sample, or body fluid. For example, a sample may include a skin sample, a cheek cell sample, saliva, or blood cells. A sample can include, without limitation, a single cell, multiple cells, fragments of cells, an aliquot of a body fluid, whole blood, platelets, serum, plasma, red blood cells, white blood cells, endothelial cells, synovial fluid, and lymphatic fluid.

In some embodiments, the mutation in the biomarker is detected before administrating the composition to identify subjects predisposed to the disease. For example, subjects with a mutation in at least one of the genes described herein are at a higher risk of contracting atherosclerosis which may lead to ischemia.

In some embodiments, the biomarkers are measured/detected after the administration. For example, the measurement may be 1-5 minutes, 1-30 minutes, 30-60 minutes, 1-2 hours, 2-12 hours, 12-24 hours, 1-2 days, 3-6 days, 1-20 weeks, or any period of time in between after the administering. In preferred embodiments, the biomarkers are measured/detected after the first effective amount of *Nigella sativa* has been administered for 1-10 weeks, 2-9 weeks, or 6-8 weeks.

In some embodiments, the method further comprises administering a second effective amount of *Nigella sativa* after the concentration of the biomarker is measured.

The second effective amount is different from the first effective amount. The second effective amount may be in a range of 0.1-1 g/kg body weight of the subject, 0.3-0.95 g/kg, 0.6-0.9 g/kg, or 0.7-0.85 g/kg. The second effective amount of *Nigella sativa* may be administered 1-3 times a day, 1-2 times/day, or preferably once a day. The second effective amount may be administered 1-4 times a week, or 2-3 times a week.

In embodiments where first and second effective amounts of *Nigella sativa* are administered, the first effective amount of *Nigella sativa* and/or the second effective amount of *Nigella sativa* is administered for 1 day or 2-10, 3-7, or 4-6 consecutive days. The duration for which the second effective amount is administered may be the same or different as the duration for the administration of the first effective amount.

The second effective amount, the administering frequency, and/or the administering duration may be adjusted according to the concentration of the biomarkers measured before and after the administration of the first effective amount. When the concentration of the biomarkers associated with angiogenesis and/or ischemia does not increase/decrease by 1-40%, 15-30%, or 20-25%, relative to the initial concentration of the biomarkers, the second effective amount is increased by 5-200%, 30-150%, 50-100% relative to the first effective amount, the administering frequency is 2-5 times, or 3-4 times more frequent than the administering frequency of the first effective amount, and/or the second effective amount is administered daily. In these embodiments, the second effective amount may range from 0.1-2 g/kg body weight, 0.3-1.9 g/kg, 0.6-1.8 g/kg, or 0.7-1.7 g/kg. When the concentration of the biomarkers associated with angiogenesis and/or ischemia increases/decreases by more than 40%, or 45-70%, or 50-60%, relative to the initial concentration of biomarkers, the second effective amount is reduced to 5-90%, 10-60%, or 15-30% relative to the first effective amount. In these embodiments, the second effective amount may range from 0.01-0.95 g/kg body weight, 0.04-0.9 g/kg, 0.07-0.85 g/kg. Also, there may be 2-5, or 3-4 fewer dosages per week of the second effective amount compared to the number of weekly dosage of the first effective amount.

In some embodiments, the administration of *Nigella sativa* is stopped once angiogenesis is effected and/or the subject is treated.

Having generally described this disclosure, a further understanding can be obtained by reference to certain specific examples which are provided herein for purposes of illustration only and are not intended to be limiting unless otherwise specified.

Example 1 Animals

Fifteen normal adult male Wistar rats (age: two months, weight: 200-300 g) were obtained from the animal house at the University of Dammam, in Dammam, Saudi Arabia. All the animals were housed individually in labelled cages with adequate ventilation and illumination, and in normal light cycle (12 light/12 dark). Normal laboratory chow and tap water were available ad libitum. The sample size was selected based on a published work with the consideration of the minimum requirement to achieve meaningful results (Chen H I, Sharma B, Akerberg B N, Numi H J, Kivelä R, Saharinen P, et al. The sinus venosus contributes to coronary vasculature through VEGFC-stimulated angiogenesis. Development. 2014 December; 141(23):4500-12. PubMed PMID: 25377552. Pubmed Central PMCID: PMC4302936, incorporated herein by reference in its entirety).

Ethical approval was provided by the ethical committee of the Deanship of Scientific Research at Dammam University with reference number IRB-2014-01-165. This committee is a branch of the National Committee of Bioethics, Saudi Arabia.

The rats were divided equally and randomly into three groups: the control group, the *Nigella sativa* (NS)-treated group, and the exercise-trained group. The NS-treated rats were given 800 mg/kg *Nigella sativa* on every weekday for eight weeks. *Nigella sativa* whole seeds were obtained from a local herb store in Dammam, Saudi Arabia. It is a product of the central region of Saudi Arabia. These seeds were previously analysed for its constituents by Al-Jassir (Al-Jassir M. Chemical composition and microflora of black cumin (*Nigella sativa* L.) seeds growing in Saudi Arabia. Food chemistry. 1992; 45(4):239-42, incorporated herein by reference in its entirety). The dose, duration and preparation of *Nigella sativa* was similar to that used by El Bahai et al., who showed cardiac hypertrophy and positive inotropic effect in the subjects after treatment. Oral administration was done via a feeding needle. A suspension of *Nigella sativa* was prepared by dissolving 10 g of freshly ground *Nigella sativa* seeds in 100 ml of distilled water. The animals in the control group were given an equivalent volume of water.

The rats in the exercise group were trained on a treadmill (IITC Life Science, five-lane rat treadmill, five days/week for eight weeks. The speed, grade and duration were progressively increased during the first week until the final protocol was achieved, with a speed of 18 m/min and an inclination of 30-32°, for a two-hour session (Barbier J, Rannou-Bekono F, Marchais J, Tanguy S, Carré F. Alterations of beta3-adrenoceptors expression and their myocardial functional effects in physiological model of chronic exercise-induced cardiac hypertrophy. Mol Cell Biochem. 2007 June; 300(1-2):69-75. PubMed PMID: 17131040, incorporated herein by reference in its entirety). An electric grid at the rear of the belt was used as the running stimulus. An equivalent volume of water was also administered to this group.

All rat groups were matched in regard to the initial and the final body weight.

Example 2 Extraction of the Hearts

Surgical extraction of the hearts was done using a longitudinal abdominal incision. Upon excision, the heart was soaked in cold Ringer's solution. Excess connective tissue and great vessels were removed. Lumens were rinsed with Ringer's solution to remove excess blood and clots. Finally, the hearts were blotted dry and weighed. The right ventricles and both atria were removed, and the remaining left ventricles were weighed. The free wall of the left ventricles was excised and stored in 4% formal-saline for histological preparation.

Example 3 Preparation of the Light Microscope Slides

The left ventricles were washed briefly in water, and then labelled and placed in a tissue processor (Tissue-Tek VIP) overnight. The specimens were dehydrated using ascending grades of alcohol: 70%, 90%, and 100% (two changes for 100% alcohol), and two changes of xylene for a period of two hours each.

The process of embedding the specimens was initiated. The specimens were impregnated in two changes of molten paraffin wax for a period of two hours for each change, and they were subsequently embedded in molten paraffin wax at a temperature of 60° C. Cassettes were used to control the position of the specimens. The wax blocks of tissues were labelled, allowed to solidify and then sectioned using microtomy (LEICA RM 2235, Leica BioSystems Buffalo Grove, Ill., USA) at a thickness of 3 µm. The sectioned tissues were floated in warm water, and then placed on microscope slides, labelled and allowed to dry.

The sections were dewaxed, washed in water and stained using the following antibodies:

a. Rat VEGF 164 affinity purified polyclonal antibody (Ab), Goat IgG (R&D Systems, Minneapolis, Minn., USA) (Lu J, Yao Y Y, Dai Q M, Ma G S, Zhang S F, Cao L, et al. Erythropoietin attenuates cardiac dysfunction by increasing myocardial angiogenesis and inhibiting interstitial fibrosis in diabetic rats. Cardiovasc Diabetol. 2012; 11:105. PubMed PMID: 22954171. Pubmed Central PMCID: PMC3527329, incorporated herein by reference in its entirety).

b. Anti-CD31 (PECAM-1) for endothelial cells to determine the density of the capillaries, purified polyclonal Ab, Goat IgG (R&D Systems, Minneapolis, Minn., USA) (Ainscough J F, Drinkhill M J, Sedo A, Turner N A, Brooke D A, Balmforth A J, et al. Angiotensin II type-1 receptor activation in the adult heart causes blood pressure-independent hypertrophy and cardiac dysfunction. Cardiovasc Res. 2009 February; 81(3):592-600. PubMed PMID: 18703536, incorporated herein by reference in its entirety).

c. Anti-von Willebrand factor (VWF) antibody, purified polyclonal Ab, Goat IgG (R&D Systems, Minneapolis, Minn., USA).

d. Anti-NOS-2 antibody stain, using a commercially available kit (Novostain Super) ABC Kit (universal), NCL-ABCu (Novocastra Laboratories, Ltd., Newcastle upon Tyne, UK).

Example 4 Estimation of the Antibody Labelling in the Light Microscopic Slides

Each specimen was stained using all the antibodies listed in Example 3. Estimation of the antibody labelling was performed using photomicrographs obtained via a digital microscope (Coolscope, Nikon Instruments Europe BV, Amsterdam Netherlands). Ten fields were selected randomly from each section. All the selected fields were clear from freezing defects, gaps or folds. The overlap of fields was clearly avoided. The slide selection and analysis was conducted by a blind operator. The sections were labelled with numbers that were unknown to the operator. The photomicrographs are shown in FIGS. 1A-1L.

Image J software was used to analyse the sections. The total labelled area in each field was measured in pixels and expressed as percentage of the total field area. The mean value of the labelled area for all fields of a specific antibody in each group was obtained (see FIG. 1 for the photomicrographs of all antibodies). Photomicrographs were analysed using ImageJ software, and the % Ab-labelled-area of 10 fields per specimen was recorded.

Example 5 Statistical Analysis Results

IBM—Statistical analysis software package—SPSS version 20 was used to analyse the data. All data were expressed as mean±SD. Analysis of variance (ANOVA) was used to compare data among the groups. The level of significance was set at p<0.05.

There was no significant difference in the weight of the heart (HW), the weight of the left ventricle (LVW), and the ratio of LVW/HW between the groups. No difference were also found between the heart weight and left ventricular weight when normalized to body weight and tibial length. (Data are not shown)

Figure 1A:
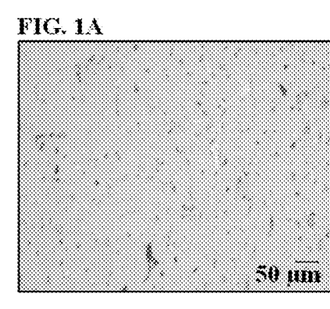
FIG. 1A is a photomicrograph of left ventricular tissues (from control rats) stained with anti-VEGF antibodies.
Figure 1B:
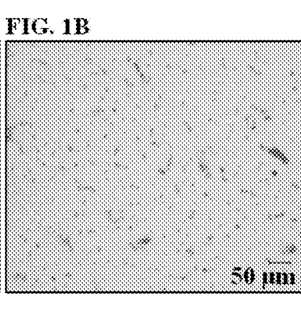
FIG. 1B is a photomicrograph of left ventricular tissues (from rats fed with *Nigella sativa*) stained with anti-VEGF antibodies.
Figure 1C:
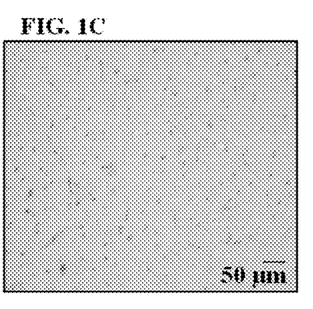
FIG. 1C is a photomicrograph of left ventricular tissues (from rats which exercised) stained with anti-VEGF antibodies.
Figure 1D:
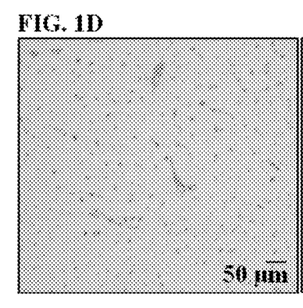
FIG. 1D is a photomicrograph of left ventricular tissues (from control rats) stained with anti-VWF antibodies.
Figure 1E:
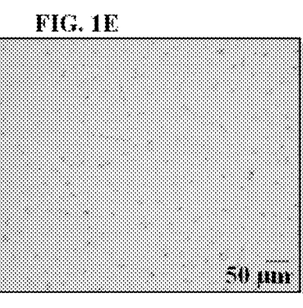
FIG. 1E is a photomicrograph of left ventricular tissues (from rats fed with *Nigella sativa*) stained with anti-VWF antibodies.
Figure 1F:
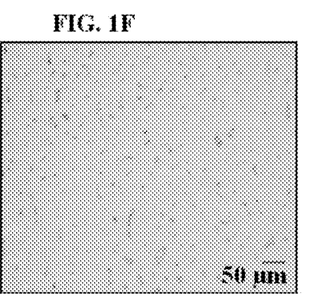
FIG. 1F is a photomicrograph of left ventricular tissues (from rats which exercised) stained with anti-VWF antibodies.
Figure 1G:
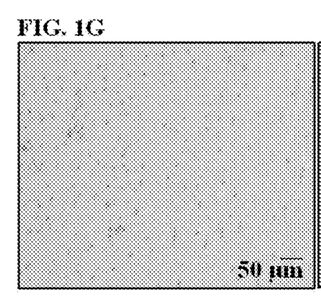
FIG. 1G is a photomicrograph of left ventricular tissues (from control rats) stained with anti-PECAM-1 antibodies.
Figure 1H:
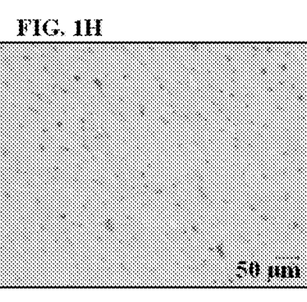
FIG. 1H is a photomicrograph of left ventricular tissues (from rats fed with *Nigella sativa*) stained with anti-PECAM-1 antibodies.
Figure 1I:
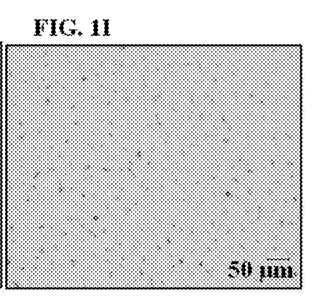
FIG. 1I is a photomicrograph of left ventricular tissues (from rats which exercised) stained with anti-PECAM-1 antibodies.
Figure 1J:
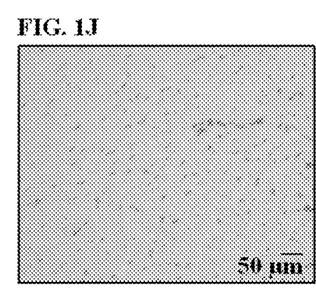
FIG. 1J is a photomicrograph of left ventricular tissues (from control rats) stained with anti-NOS-2 antibodies.
Figure 1K:
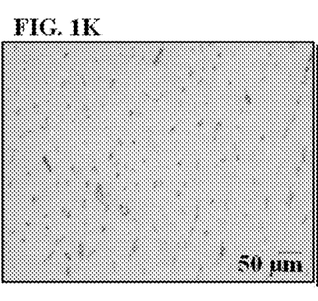
FIG. 1K is a photomicrograph of left ventricular tissues (from rats fed with *Nigella sativa*) stained with anti-NOS-2 antibodies.
Figure 1L:
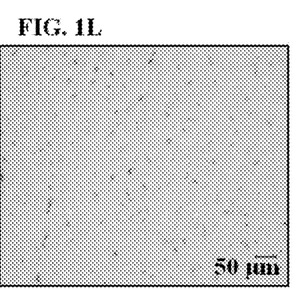
FIG. 1L is a photomicrograph of left ventricular tissues (from rats which exercised) stained with anti-NOS-2 antibodies.
Figure 2A:
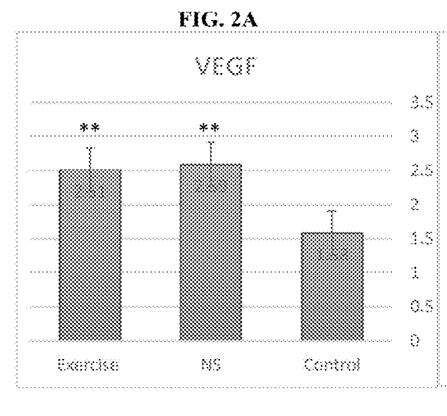
FIG. 2A compares the levels of VEGF between the rats.

FIG. 2A shows the levels of VEGF are significantly higher in the Nigella-fed (2.59±1.37) and the exercise (2.51±1.86) groups compared to the control group (1.58±0.78) ("**" indicates P<0.01). The levels of VEGF were comparable in the Nigella-fed and the exercise-trained groups, indicating that both Nigella sativa administration and exercise training were potential factors for induction of capillary growth.

Figure 2B:
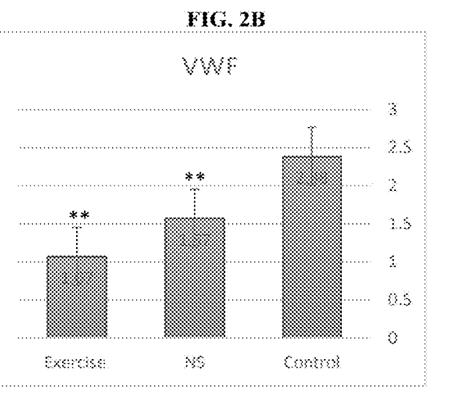
FIG. 2B compares the levels of VWF between the rats.

FIG. 2B shows the levels of VWF are significantly lower in the Nigella-fed (1.57±0.83) and the exercise (1.07±0.72) groups compared to the control group (2.38±1.72) ("**" indicates P<0.01). This finding might support the angiogenic effect of both long-term administration of Nigella sativa and exercise on coronary circulation. The observation also supported the similarities in the actions of these two interventions.

Figure 2C:
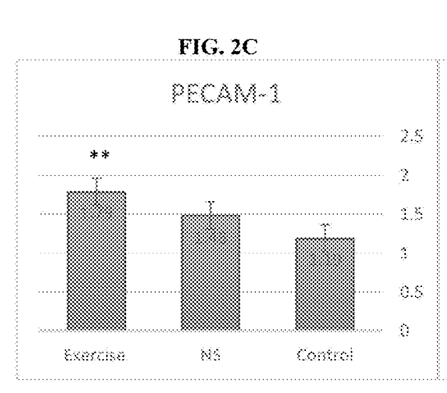
FIG. 2C compares the levels of PECAM-1 between the rats.
Figure 2D:
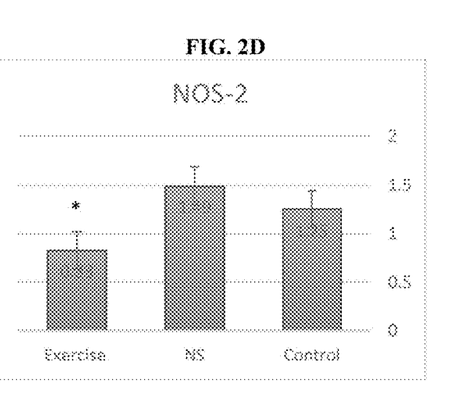
FIG. 2D compares the levels of NOS-2 between the rats.

FIGS. 2C and 2D show the exercise group was found to have a higher level of PECAM-1 (1.79±0.78) and a lower level of NOS-2 (0.83±0.57) than the control group (PECAM-1: 1.19±1.17, "**" indicates P<0.01; NOS-2: 1.25±1.19, "*" indicates P<0.05). The exercise protocol might be too mild to induce a significant increase in NOS-2 levels in the heart. The training did not demonstrate an increase in the expression of NOS-2 in the cross-section of the left ventricles of the exercise-trained rats. Interestingly, upregulation of NOS-2 was clearly elucidated in the hindlimb of the rats after femoral artery ligation and reperfusion. Rats fed with Nigella sativa did not show an increase in NOS-2. Nigella sativa is known to be an anti-inflammatory and antioxidant mediator and it might not culminate in overexpression of NOS-2.

The rats fed with Nigella sativa did not demonstrate a significant increase in PECAM-1. However, the possibility of the presence of ongoing capillary angiogenesis may still be valid because there was a statistically significant increase in the VEGF level and a statistically significant decrease in the VWF level. A longer duration of Nigella administration might be required to achieve a higher capillary bed density which is indicated by elevated PECAM-1 levels. By stopping the administration of Nigella sativa during the weekends may have delayed the onset of cardiac hypertrophy in the rats. Different stages of cardiac and coronary adaptation to exercise training have also been reported (Gielen S, Schuler G, Adams V. Cardiovascular effects of exercise training: molecular mechanisms. Circulation. 2010 September; 122(12):1221-38. PubMed PMID: 20855669, incorporated herein by reference in its entirety).

The disclosure demonstrated evidence of active coronary angiogenesis induced by administration of Nigella sativa and aerobic exercise training in adult Wistar rats. This evidence includes a statistically significant increase in the VEGF level and a reduction in the VWF level. This finding is promising in the emergence of new therapeutic and preventive strategy for coronary artery disease in specific and other peripheral artery diseases in general.

The invention claimed is:

1. A method for effecting active coronary angiogenesis in a patient having ischemic heart disease comprising:
administering to said patient over a period of 4 to 52 weeks a first effective amount of Nigella sativa, thereby inducing active coronary angiogenesis in said patient.

2. The method of claim 1, wherein the Nigella sativa is in a form of seeds or ground seeds.

3. The method of claim 1, wherein the ischemic heart disease is myocardial infarction.

4. The method of claim 1, wherein the ischemic heart disease is selected from the group consisting of stable angina, cardiac syndrome X, and cardiac arrest.

5. The method of claim 1, which effects active coronary angiogenesis in the heart of the patient and does not induce cardiac hypertrophy.

6. The method of claim 1, wherein the first effective amount of Nigella sativa is administered in a composition comprising water and Nigella sativa seeds.

7. The method of claim 6, wherein the composition comprises 1-50 wt % Nigella sativa seeds, based on a total weight of the composition.

8. The method of claim 7, wherein the administering comprises administering 0.1 to 1 g of Nigella sativa seeds per kg of body weight.

9. The method of claim 1, wherein the first effective amount of Nigella sativa is administered 1-3 times a day.

10. The method of claim 1, wherein the first effective amount of Nigella sativa is administered for 6-30 weeks.

11. The method of claim 10, wherein the first effective amount of Nigella sativa is administered 4-6 days per week for 7-10 weeks.

12. The method of claim 11, wherein the first effective amount of Nigella sativa is administered for 4-6 consecutive days per week.

13. The method of claim 1, wherein the first effective amount of Nigella sativa is in a range of 0.1-1 g/kg body weight of the subject.

14. The method of claim 13, wherein the first effective amount of Nigella sativa is in a range of 0.6-0.9 g/kg body weight of the subject.

15. The method of claim 1, wherein the first effective amount of Nigella sativa is administered orally.

16. The method of claim 1, further comprising measuring a level of at least one biomarker selected from the group consisting of VEGF, VWF, PECAM-1, and NOS-2 before and/or after the administering of the first effective amount.

17. The method of claim 16, further comprising:
administering a second effective amount of Nigella sativa.

18. The method of claim 17, wherein the second effective amount of Nigella sativa is in a range of 0.1-1 g/kg body weight of the subject and is different from the first effective amount of Nigella sativa.

19. The method of claim 17, the second effective amount of Nigella sativa is administered for 1 day or 2-10 consecutive days.

20. The method of claim 19, wherein the second effective amount of Nigella sativa is administered for 4-6 consecutive days.

* * * * *